(12) United States Patent
Krause et al.

(10) Patent No.: US 6,702,760 B2
(45) Date of Patent: Mar. 9, 2004

(54) BIOPSY AND COAGULANT DEVICE

(75) Inventors: William R. Krause, Charlottesville, VA (US); Francis C. Classe, New York, NY (US)

(73) Assignee: Bioengineering Consultants, Charlottesville, VA (US)

( * ) Notice: Subject to any disclaimer, the term of this patent is extended or adjusted under 35 U.S.C. 154(b) by 90 days.

(21) Appl. No.: 10/008,417

(22) Filed: Nov. 6, 2001

(65) Prior Publication Data

US 2002/0099307 A1 Jul. 25, 2002

Related U.S. Application Data

(60) Provisional application No. 60/246,029, filed on Nov. 6, 2000.

(51) Int. Cl.[7] .............................................. A61B 10/00
(52) U.S. Cl. ....................... 600/564; 600/566; 600/567; 606/167; 606/213; 606/214
(58) Field of Search ............................. 600/565, 564, 600/566, 568, 567; 606/167, 168, 169, 170, 213, 214

(56) References Cited

U.S. PATENT DOCUMENTS

| | | | | |
|---|---|---|---|---|
| 5,479,936 A | * | 1/1996 | Nabai et al. | 600/567 |
| 6,099,550 A | * | 8/2000 | Yoon | 606/205 |
| 6,280,399 B1 | * | 8/2001 | Rossin et al. | 600/567 |
| 2002/0016612 A1 | * | 2/2002 | Ashby et al. | 606/213 |
| 2003/0009194 A1 | * | 1/2003 | Saker et al. | 606/213 |

* cited by examiner

*Primary Examiner*—Max F. Hindenburg
*Assistant Examiner*—Jonathan Foreman
(74) *Attorney, Agent, or Firm*—Sheldon H. Parker

(57) ABSTRACT

The biopsy device has a biopsy channel connected to an aspiration and collecting chamber and at least one application channel connected to a dispensing chamber integrally connected with the aspiration chamber. The application channel is formed by a tube centrically slipped over the biopsy channel wall. To enable the collection of tissue specimens without tissue specimens entering and obstructing the application cannula, the distal segment of the application channel forms a close fitting and concentric sheath around the biopsy channel. The proximal end of the application channel has a larger diameter than the distal end allowing for unobstructed flow of the application material past the biopsy channel wall upon retraction of the biopsy channel from the distal segment of the application channel.

11 Claims, 11 Drawing Sheets

BIOPSY AND COAGULANT DEVICE

This application claims the benefit of provisional application No. 60/246,029, filed Nov. 6, 2000.

FIELD OF THE INVENTION

The present invention relates to a biopsy device that takes a biopsy sample of human or animal tissue and delivers a coagulant or other material to the biopsy incision track in order to plug the track and prevent bleeding.

BACKGROUND OF THE INVENTION

Excision biopsy of the liver has traditionally been the gold standard for assessing the extent of injury and determining prognosis in chronic viral hepatitis and liver cancer. A significant complication that frequently occurs is bleeding from the biopsy site. Significant hemorrhage occurs in 0.35 to 0.5% of all procedures while evidence of sub-clinical bleeding, as detectable by ultrasound 24 hours post biopsy, has been reported in up to 23% of patients. Smaller amounts of surface bleeding is almost universal and is frequently associated with mild to moderate pain.

Excision biopsies from other organs, such as the lungs, also exhibit a relatively high complication rate due to hemorrhagic incidents and pneumothorax. Also with kidney biopsies and biopsies of other organs, perfuse bleeding is considered the most important complication.

The most common liver biopsy technique is by percutaneously inserting a needle into the liver for a fraction of a second and obtaining a tissue sample. The subsequent procedure for taking the biopsy varies according to whether the biopsy needle is of the aspiration or cutting type. For the cutting needle, the needle is inserted into the liver and followed by the outer sheath. The specimen is entrapped in the recessed section of the cutting needle. The aspiration technique is probably the most widely used technique. The best known aspiration biopsy technique is based on the principle indicated by Menghini. There a hollow needle having an average diameter of 1.4 mm and having a facility for attachment of a syringe is used, by which a negative pressure (suction) is applied upon piercing through the skin and prior to the organ puncture proper. The organ puncture (liver) then is realized with a sustained suction to secure the biopsy sample.

In order to obviate the reported complications, it was recommended to subsequently plug the needle track with resorbable material so as to eliminate, in particular, bleeding complications. Such techniques, however, imply a long residence time of the puncture needle in the organ, which again constitutes a cause of complications, in particular with liver punctures.

From Austrian Pat. No. 384,165, a biopsy needle device of the initially defined kind is known, with which the cannula has a curved partition wall towards the internal limitation of the cannula lumina. Therein, the partition wall does not reach immediately to the front end of the cannula so that the biopsy channel and the application channel communicate in the region of the tip of the cannula. The multi-lumen biopsy needle according to Austrian Pat. No. 384,165 enables the collection of tissue and the application of substances plugging the puncture track in coordination with the puncturing procedure in one operating cycle, thus largely shortening the time of intervention.

U.S. Pat. No. 4,850,373 and related EP patents 243341 A, B1 etc., also describes a biopsy needle device having a two lumen cannula, a biopsy channel of constant cross section and one application channel. The application channel is formed by a tube eccentrically slipped over the biopsy channel wall. Furthermore, the biopsy channel is described as a noncircular tubular structure with its channel wall flattened in cross section such that an application channel is formed between the flattened side of the biopsy channel wall and the outer application tube. In addition, surface contact exists between the non-flattened side of the biopsy channel wall and the application tube.

A common surgical material used to control bleeding is Gelfoam®. Gelfoam® is supplied in either a powder form or as an implantable sponge. Sterile sponges, such as Gelfoam®, are prepared in dry sterile sheets that are used as packing material during surgery for control of bleeding. The sponge sheets are left in the surgical site after surgery to stop bleeding and are absorbed by the body in 1 to 6 weeks. A number of techniques have used these absorbable sterile sponge materials to plug a biopsy track to minimize or prevent bleeding. The absorbable sponge provides a mechanical blockage of the track, encourages clotting, and minimizes bleeding though the biopsy track. Despite the advantages of using absorbable sponge to plug a biopsy track this technique has not achieved widespread use because of difficulty in preparing and delivering the sponge material into the biopsy track.

One example of a biopsy wound closure device using an implantable sponge is described in U.S. Pat. No. 5,388,588. According to this patent, a circular sponge of an absorbable foam material is precut and inserted into a biopsy site by an applicator rod having the sponge positioned on the end. Once the sponge is implanted, the sponge absorbs blood and swells to fill the track preventing further bleeding at the biopsy site. However, the sponge is difficult to deliver and expands slowly once delivered. In addition, this delivery method can only deliver a sponge of a limited size that provides less local compression than desired and may incompletely fill the target site. Further, bleeding may continue along sections of the biopsy track where no sponge has been delivered.

Another example of a Gelfoam® inserting device to facilitate hemostasis is described in U.S. Pat. No. 6,086,607. According to this patent, a method of cutting a piece of Gelfoam® sponge from a sheet of the material, folding the strip to form a pledget with one end of different cross section than the other end, and inserting the pledget in an adapter to compress the pledget and for attachment to a syringe for delivery of the pledget to the tissue. The adapter is attached to a cannula that was previously inserted into the organ being biopsied and the Gelfoam® is inserted into the tissue through the cannula.

No previous patents describe the combination of the multi lumen needle containing a biopsy channel and an application channel with a syringe assembly for obtaining the biopsy and delivering the application material. In addition, the prior art does not describe a biopsy needle that translates within the application tube so that the application material will have an unobstructed passage into the biopsy track. The previous patents either describe the biopsy channel as being eccentrically positioned within the application tube as opposed to the disclosed concentric positioned biopsy or a separate device which delivers a hemostatic sponge to the biopsy track.

SUMMARY OF THE INVENTION

The present invention provides a biopsy device with a view to enabling the collection of tissue specimens for biopsy and to apply auxiliary substances directly in the site of the puncture without tissue specimens getting into the application cannula, thus obstructing the same.

In accordance with one aspect of the present invention, a syringe system comprised of a multi chambered unit for taking the biopsy specimen and delivering a coagulating material. The system includes a multi-lumen channel structure with at least one biopsy channel of formed by a tube constant cross section over its entire length and at least one application channel formed by a tube of varying cross section slipped over the biopsy channel wall. The biopsy tube is connected to the end of biopsy syringe and opens to the inner chamber of the system for securing and retrieving the biopsy specimen. The application tube is connected to the end of the outer casing and communicates with the outer chamber containing the application material. When the biopsy syringe is retracted within syringe assembly, the biopsy needle is also retracted within the application channel.

The biopsy channel wall projecting out of the application tube with its cutting edge formed by an acute angularly designed end of the biopsy wall channel.

Using a prior art biopsy device, a biopsy is achieved according to the invention in that after the tissue specimen is collected in the biopsy channel, the inner tube containing the tissue specimen is retracted within the concentric outer application tube thus allowing the application material to be injected into the biopsy track without obstruction. The retraction of the inner, biopsy tube provides the mechanism by which the application material is forced to be expelled from the outer application tube. This is facilitated according to the invention by a placing the biopsy device in another device which causes the translations and movements of the parts of the fore mentioned biopsy device.

DETAILED DESCRIPTION OF THE PREFERRED EMBODIMENTS

The system of the present invention collects and retrieves a biopsy specimen and then delivers, without removal of the biopsy assembly, an absorbable coagulant material to facilitate hemostasis of the biopsy track or other puncture wound in a simple and safe manner. The apparatus for collecting the biopsy specimen and delivering a coagulant material will be described below in connection with procurement of a liver biopsy sample for the diagnosis of liver diseases. However, the invention can be used for the procurement of other biopsy specimens from other vascular organs as well as facilitating hemostasis of other types of puncture wounds or tissue access tracks to prevent bleeding of these wounds.

The system 10, for procuring a biopsy specimen and delivering a coagulant material, includes a multi-chambered syringe assembly 100 for procuring the biopsy, storing the biopsy specimen and coagulant material, and delivering the coagulant material. The system 10 also includes a delivery assembly 500 to enable the operator to manipulate the syringe components for securing the biopsy specimen and dispensing the coagulant material.

Figure 1:
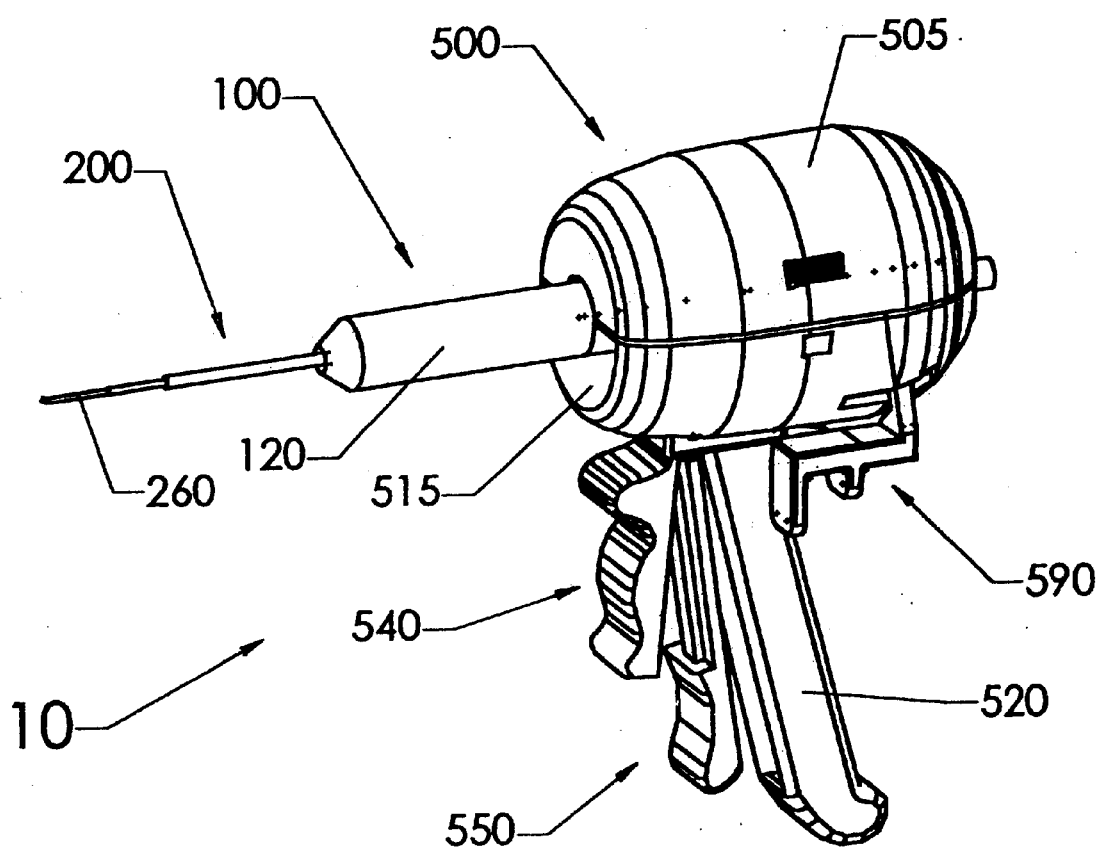
FIG. 1 is a perspective view of the assembled biopsy (syringe) and delivery device according to the invention.
Figure 2:
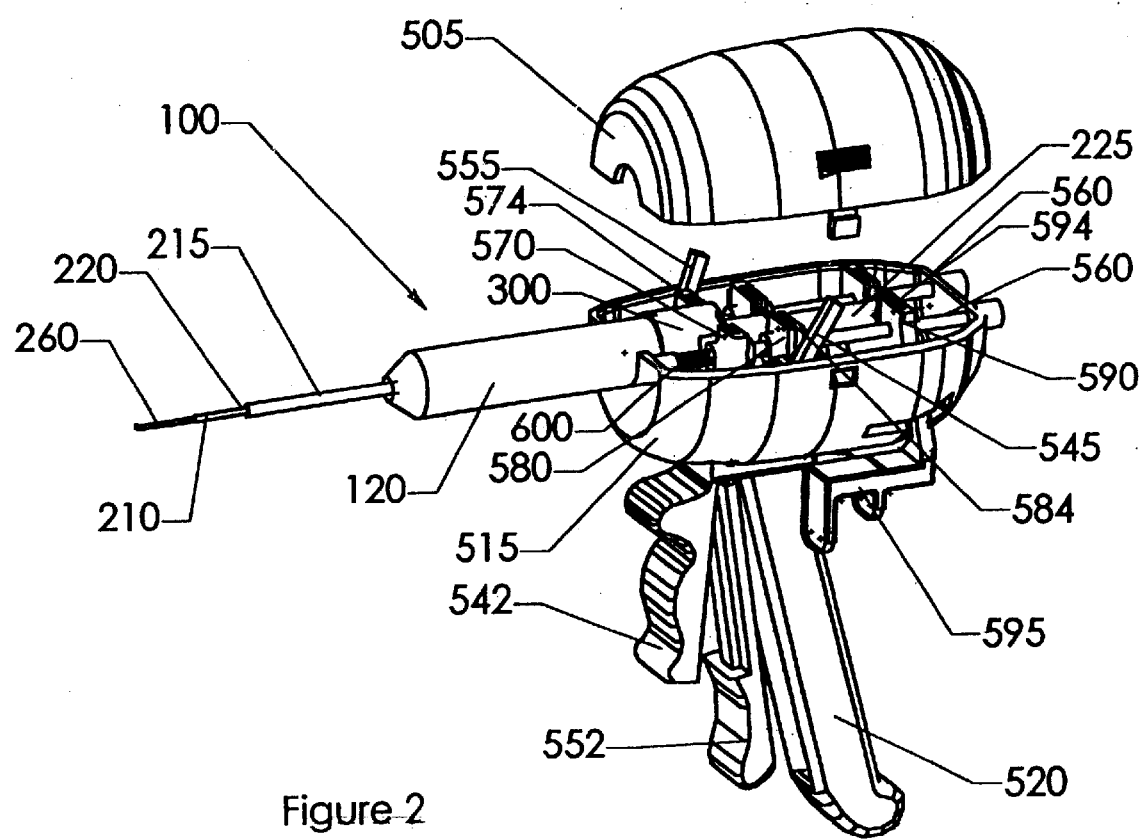
FIG. 2 is a perspective view of the delivery system with the top removed.
Figure 3A:
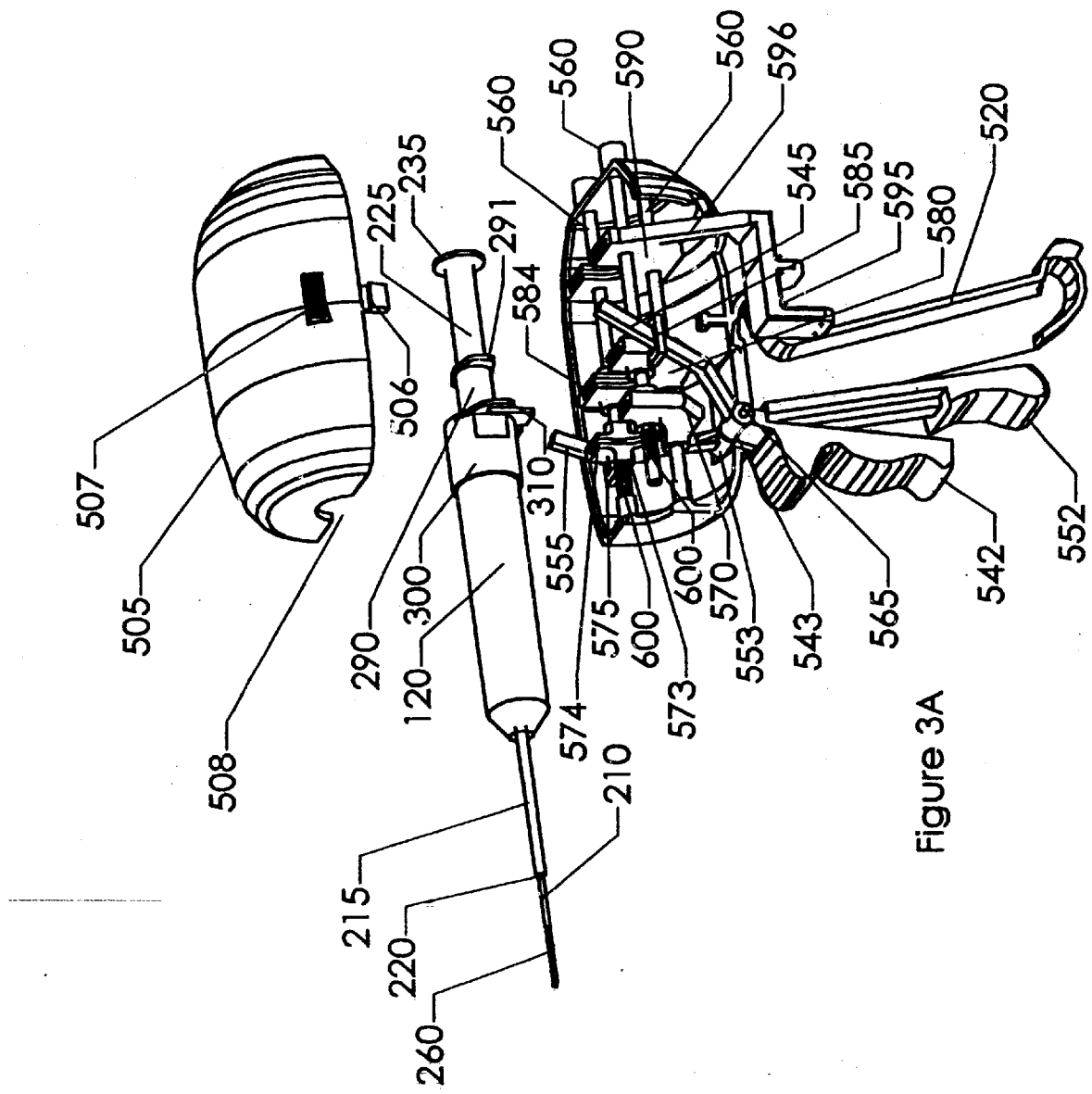
FIG. 3A is a cut-away perspective view of the delivery device with the biopsy syringe unit separated from the delivery device.
Figure 3B:
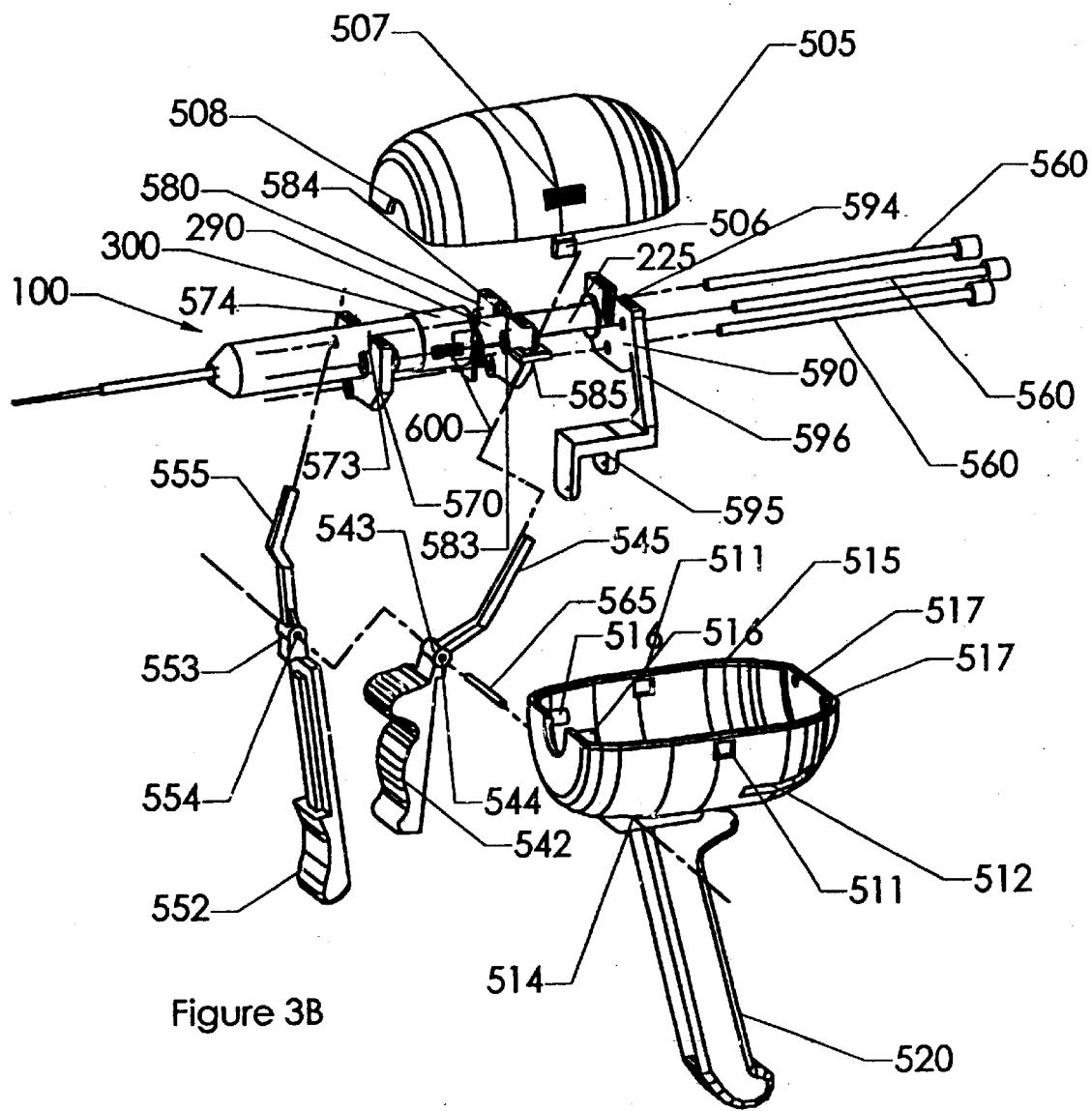
FIG. 3B is an exploded perspective view of the delivery system parts.
Figure 3C:
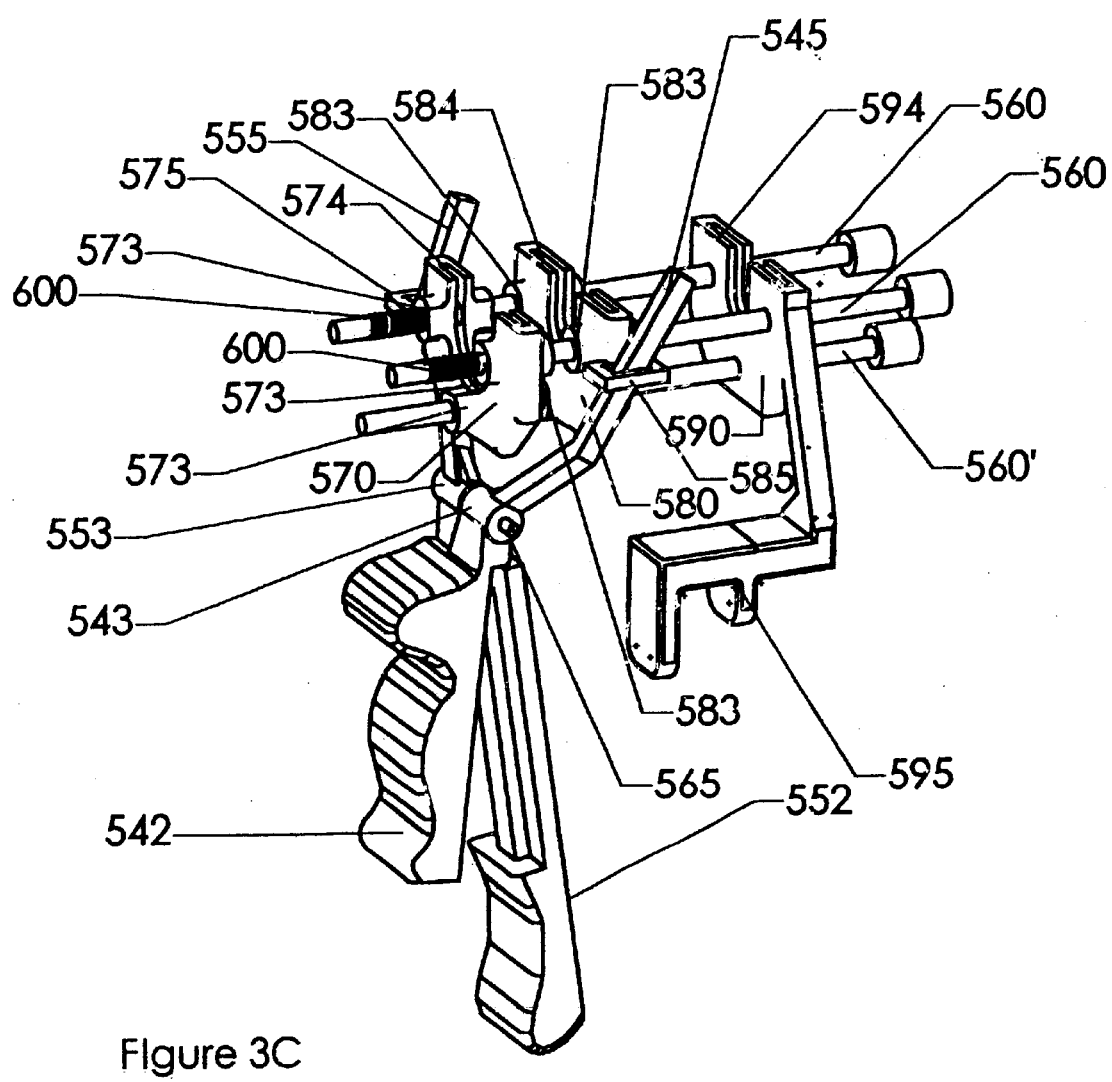
FIG. 3C is a perspective view of the slide mechanism for the delivery system.

FIG. 1 illustrates the assembled device 10 of the invention including the syringe assembly 100 and the delivery assembly 500. The delivery assembly 500 consisting of the top shell 505, bottom shell 515, handle 520, triggers 540, 550 and rear slide 590.

FIGS. 2, 3A, 3B and 3C illustrate an overall view of the two assemblies of the invention with the top shell 505 removed. For removal, projections 507 are squeezed inward to release the tabs 506 from the holes 511. The top shell 505 is mated to the bottom shell 515 by inserting tabs 506 into holes 511 such that opening 508 is positioned over the barrel 120 of the syringe unit 100. When viewed from the outside, the syringe unit 100 is comprised the outer casing 120, the needle sheath 200, the biopsy needle 260, the outer casing top 300, the coagulant plunger 290, and the biopsy plunger 225. The interior of the syringe assembly 100 is disclosed hereinafter. The syringe assembly 100 is positioned within the delivery unit 500 by inserting the flange 310 of the outer casing top 300 into the slot 574 of the front slide holder 570. The flange 291 of the coagulant plunger 290 is inserted into the slot 584 of the middle slide holder 580 and the flange 235 of the biopsy plunger 225 is inserted into the slot 594 of the rear slide holder 590. The movement of the syringe parts is accomplished by the slide holders 570 and 580 which are manually operated by triggers 540, 550, respectively, and rear slide holder 590 which is positioned using the operator's thumb on handle 595. The extension arm 555 of the primary trigger 552 is positioned within the yoke 575 of the front slide holder 570 containing the outer casing top 300. When the trigger 542 is rotated towards the handle 520, the extension arm 555 contacts the forward portion of the yoke 575 and moves the front holder 570 and syringe outer casing 300 forward along the slide pins 560 mounted within the bottom shell 515. The slide pins 560 have helical springs 600 placed over them. The springs 600 are positioned between the front slide holder 570 and the wall of the bottom shell 515. The springs 600 are dimensioned to place sufficient pressure against the front slide holder 570 to place it in the open position, as illustrated in FIG. 1, when not under user applied pressure. Likewise, the extension arm 545 of the biopsy trigger 542 is positioned within the yoke 585 of the holder 580 so that when the trigger 542 is pulled toward the handle 520 the extension arm 545 contacts the forward portion of the yoke 585 and moves the holder 580 and the coagulant plunger 290 forward along the slide pins 560. The collars 573, 583 on the holders 570, 580, respectively prevent the holders from tilting and jamming.

During the normal operation of the device, the two triggers 540, 550 would be in an open position; rotated away from the handle 540. With the syringe filled with saline and coagulant for taking a biopsy, the syringe unit 100 is placed in the delivery assembly 500 as described above. The syringe flanges 235, 291 and 310 are inserted into holder slots 594, 583 and 574, respectively.

The needle 260 and needle sheath 200 are driven through the skin and underlying tissue into the abdominal cavity. With his thumb on the back holder extension 595, the operator the pushes the extension to flush the needle 260 with saline contained in the biopsy chamber 295. The assembly is advanced forward until the operator feels the tip of the needle 260 penetrate the organ to be biopsied. The operator then pulls back on the back holder extension 595 to provide a slight amount of negative pressure within the biopsy chamber 295 and to hold the surface of the tissue in the biopsy needle channel. The coagulant trigger handle 542 of the trigger 540 and biopsy trigger handle 552 of the trigger 550 are fixed to the lower shell 515 by a pin 565 extending through fulcrum 543 and fulcrum 553, respectively. The extension arm 545 of coagulant trigger 540 penetrates yoke 585 to control the movement of holder 580. Likewise extension arm 555 of trigger 550 intersects with yoke 575 of holder 570. The trigger handles 542 and 552 are squeezed toward the handle 520, which advances the syringe assembly 100 forward, and the needle 260 advances deeper into the tissue. The coagulant trigger 540 is released which pulls the coagulant plunger 290 backwards. Retraction of the coagulant plunger 290 forces the coagulant from the middle chamber 136 to the outer chamber 135 and out though the needle sheath 200 as the biopsy needle 260 is withdrawn. Although the inner-outer sheath combination has been described in the prior art, this has only been in conjunction with fixed structures. The complexities of having movable cannulas have not been resolved until the disclosed system.

Figure 4:
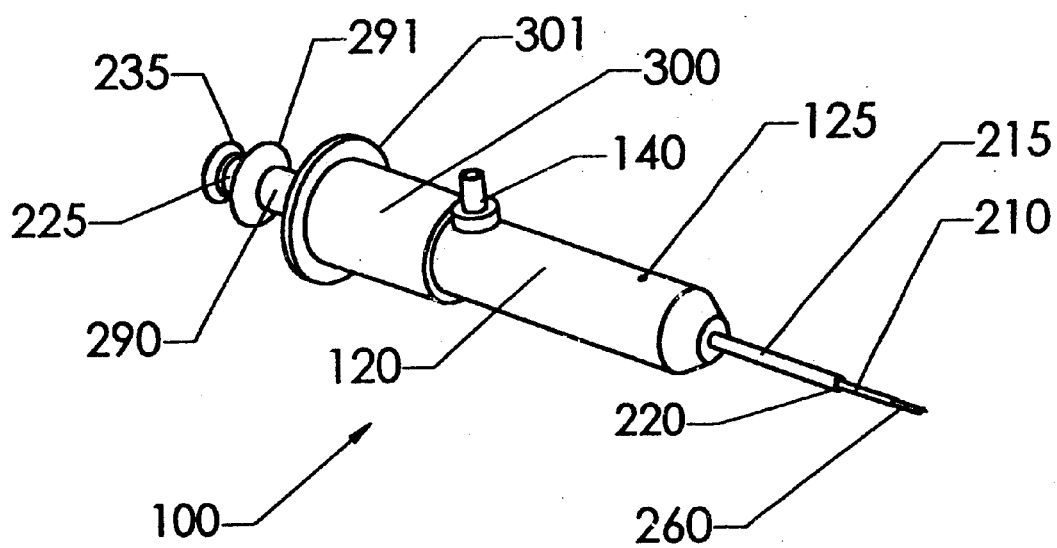
FIG. 4 is a perspective view of the biopsy syringe.

The syringe unit can be also be used independently to obtain a biopsy sample and deliver the coagulant plug. In this embodiment the operation of the syringe is done manually. FIG. 4 illustrates the outer view of the syringe assembly 100 according to the invention and as used independently from the delivery system. The biopsy needle 260 extends from the needle sheath 200 attached to the outer casing 120. The needle sheath 200 has three distinct regions, a distal segment 210 which has an internal diameter slightly greater than the outer diameter of the biopsy needle 260, a proximal region 215 that has a substantially larger diameter than the distal segment 210 and a transition segment 220 between the two. The outer casing top 300 provides for concentric guiding of the inner coagulant cylinder 290, which in turn guides the biopsy plunger 225. A one-way check valve 140 is located on the outer casing 120 for filling the syringe with coagulant material. A vent hole 125 is also located on the far end of the outer case to allow operation of the coagulant plunger.

Figure 5A:
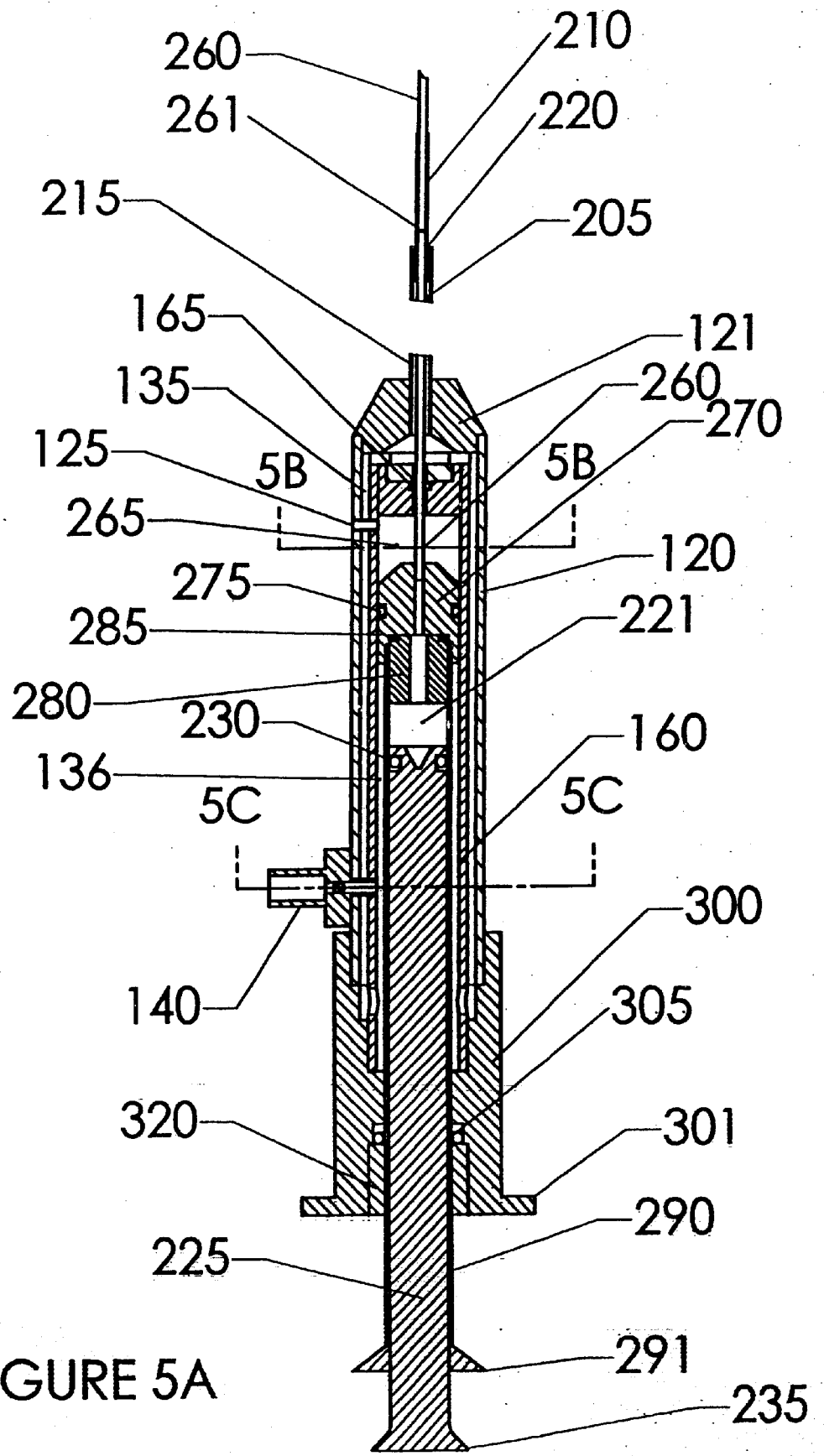
FIG. 5A is a longitudinal, sectional view of the biopsy syringe.
Figure 5B:
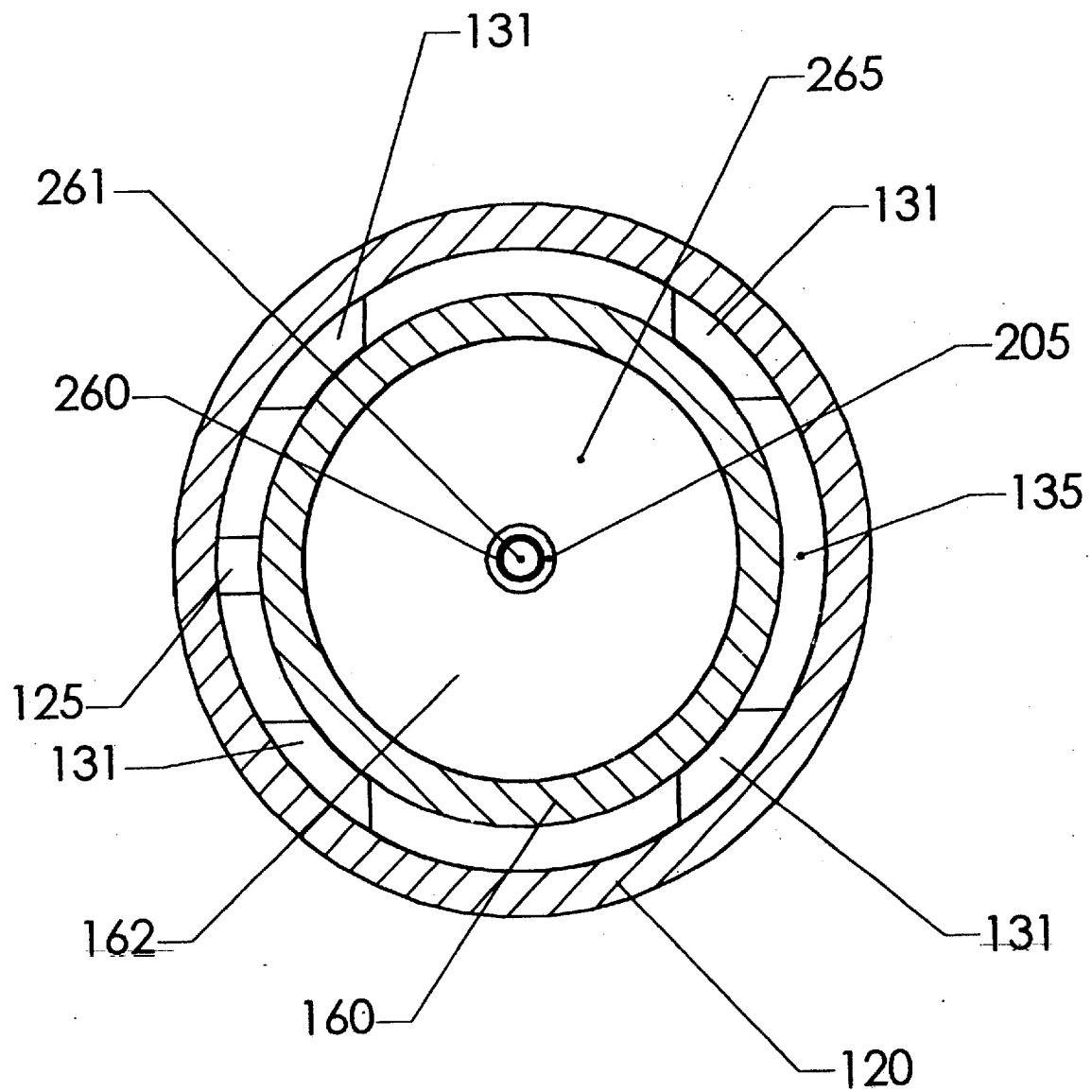
FIG. 5B is a cross sectional end view of the biopsy syringe taken about plane 5B—5B of FIG. 5A.
Figure 5C:
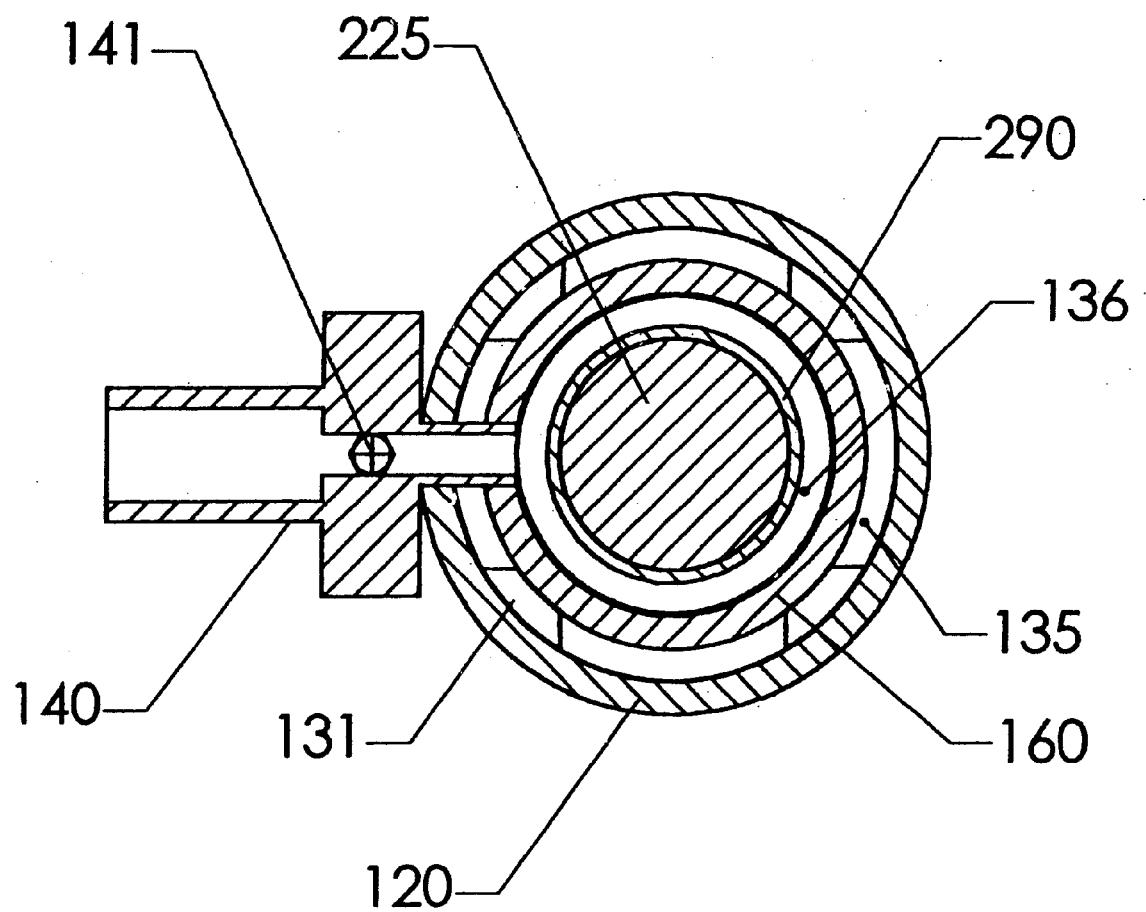
FIG. 5C is a cross sectional view of the biopsy syringe taken about plane 5C—5C of FIG. 5A.
Figure 5D:
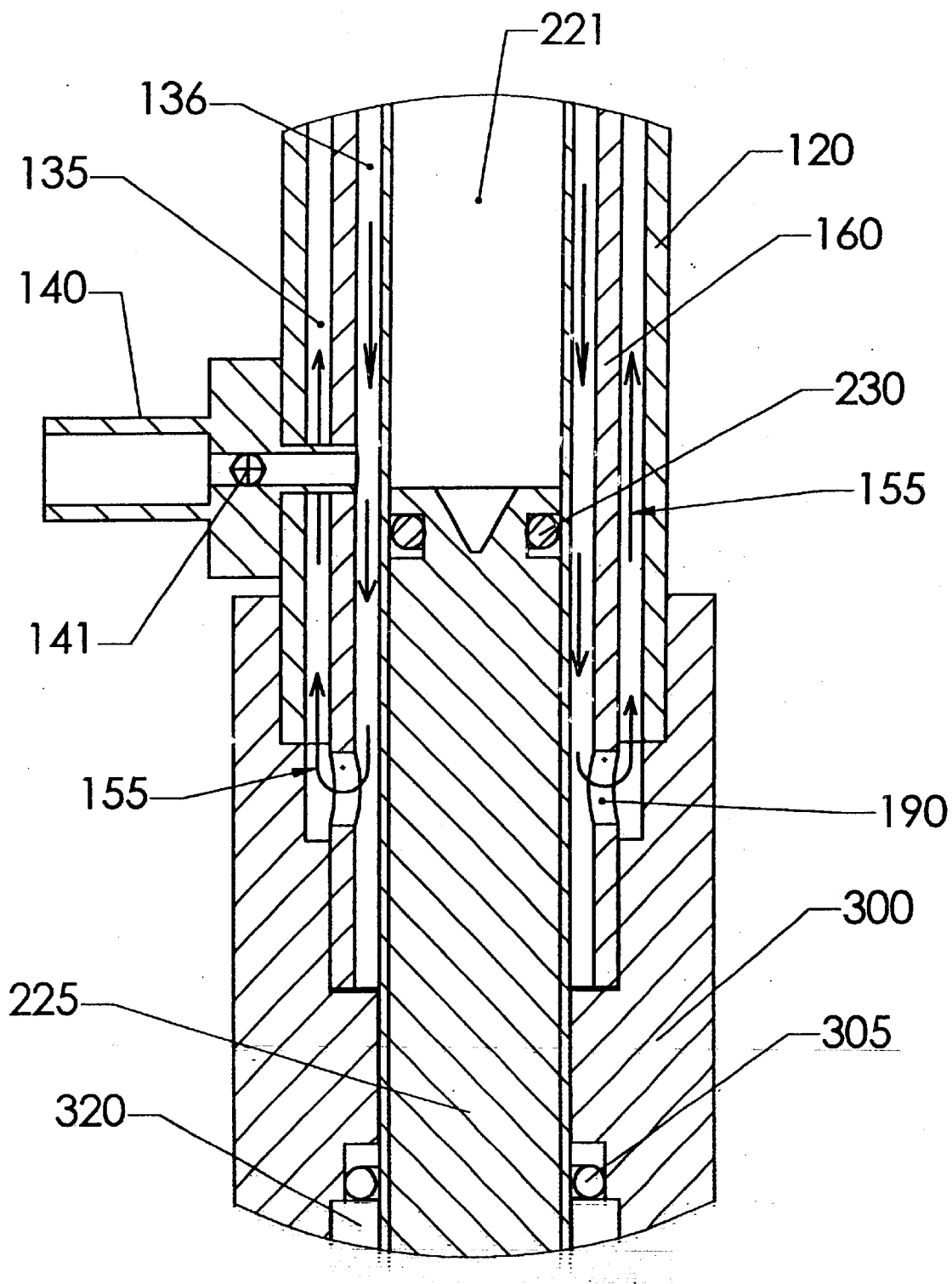
FIG. 5D is a sectional view of the near end of the biopsy syringe showing the direction of flow of the coagulant material upon retraction of the coagulant plunger.
Figure 5E:
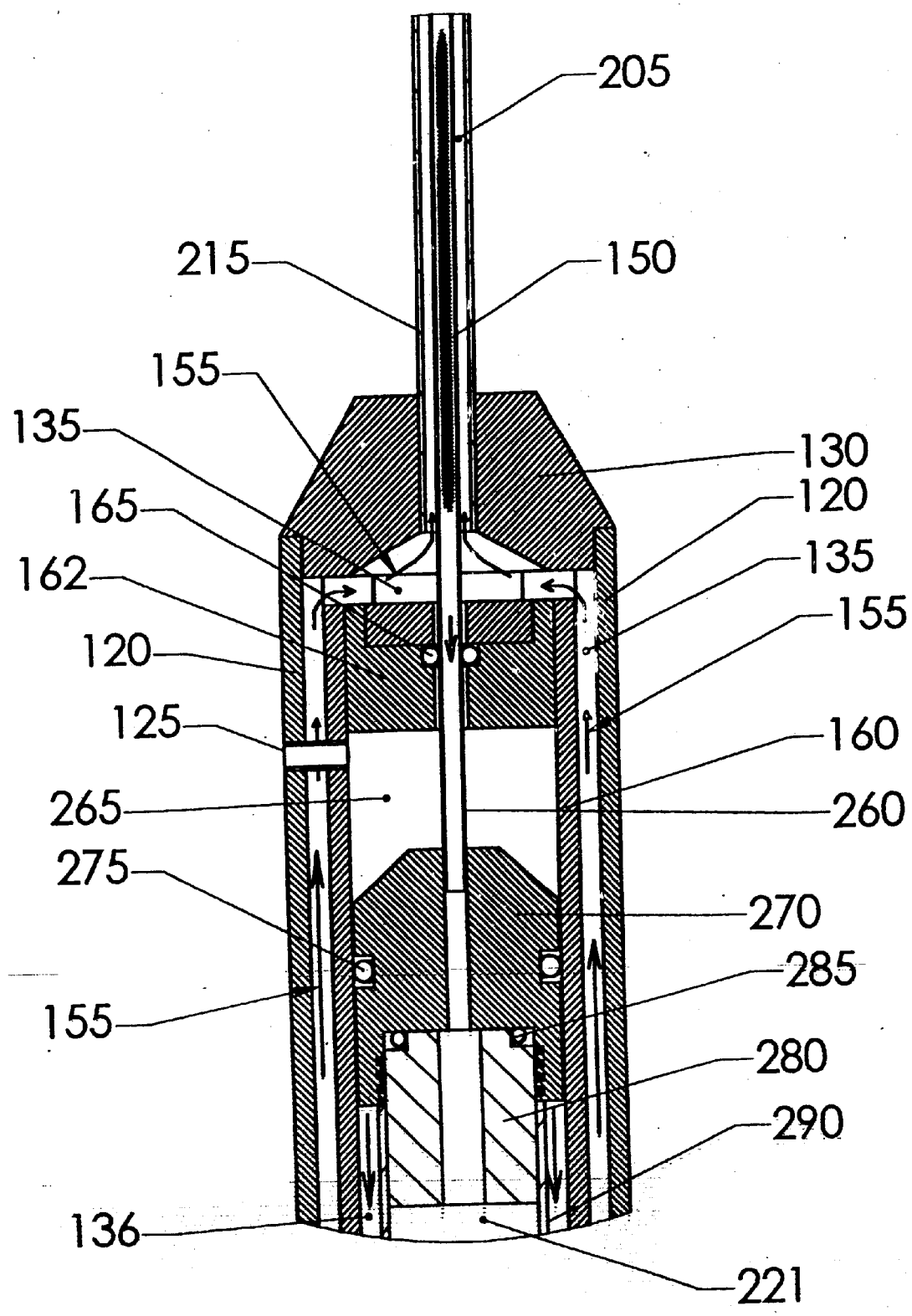
FIG. 5E is a sectional view of the far end of the biopsy syringe showing the direction of flow of the coagulant material and the biopsy specimen.

The syringe assembly is illustrated in more detail in FIGS. 5A–5E. FIG. 5A shows a longitudinal cut away view of the syringe assembly 100. The biopsy needle 260 is attached to the distal end 270 of the coagulant plunger 280. The channel 261 of the biopsy needle 260 is in fluid communication with the biopsy chamber 221. The biopsy chamber 221 is formed with the coagulant plunger 280 at the distal end and the biopsy plunger 225 at the proximal end. The biopsy needle 260 passes through an o-ring 165 at the distal end of the inner coagulant cylinder 160 to provide a seal between the outer coagulant chamber 135 and the inner air chamber 265. The biopsy plunger 225 slides within the coagulant cylinder 290. The coagulant cylinder 290 is guided within the assembly at the proximal end by the outer casing top 300 and the insert 320. The o-ring 305 provides a watertight seal within the outer casing top 300, distal to the insert 320. At the distal end 270, the coagulant cylinder 290 is attached to the coagulant plunger 280, which is guided within the assembly by the middle coagulant cylinder 160. The o-ring 275 in the coagulant plunger 280 forms a seal for the middle coagulant cylinder 160 to provide a seal between the inner coagulant chamber 136 and the air chamber 265. The inner coagulant chamber 136 is bounded at the proximal end by the outer casing top 300 that supports the near end of the inner coagulant cylinder 290. The distal end of the middle coagulant cylinder 160 containing the end 162 is supported by spacers 131 of the outer casing end. the inner air chamber 265. The biopsy plunger 225 slides within the coagulant cylinder 290. The coagulant cylinder 290 is guided within the assembly at the proximal end by the outer casing top 300 and the insert 320. The o-ring 305 provides a watertight seal within the outer casing top 300, distal to the insert 320. At the distal end, the coagulant cylinder 290 is attached to the coagulant plunger 270, which is guided within the assembly by the middle coagulant cylinder 160. The oaring 275 in the coagulant plunger 270 forms a seal for the middle coagulant cylinder 160 to provide a seal between the inner coagulant chamber 136 and the air chamber 265. The inner coagulant chamber 136 is bounded at the proximal end by the outer casing top 300 that supports the near end of the inner coagulant cylinder 160. The distal end of the middle coagulant cylinder 160 containing the end 162 is supported by spacers 131 of the outer casing end 130, thus forming the coagulant chamber 135. Passageways 190, as illustrated in FIG. 5D, within the middle coagulant cylinder 160 allows communication between the inner coagulant chamber 136 and the outer coagulant chamber 135 formed by the outer casing 120. An air vent 125 is positioned at the far end of the chamber 265 in front of the coagulant plunger 270 to enable air to enter or escape from the chamber 265 as the plunger 270 moves back and forth. The check valve 140 allows the filling of the inner and outer coagulant chambers 136, 135 respectively with coagulant. The one-way valve 141 only allows insertion of the fluid and prevents fluid from escaping through the check valve 140 during operation. The needle sheath 200 is attached to the end unit 121 of the outer casing 120 such that the interior channel 205 of the sheath 200 communicates with the outer coagulant chamber 135 at the distal end of the inner coagulant cylinder 160.

The operation of the syringe assembly 100, method of filling the syringe and obtaining a biopsy are as disclosed herein or through any other method obvious to those skilled in the art when incorporated with this disclosure. The biopsy plunger 225 and coagulant plunger 290 are fully inserted into the lower assembly 500. The biopsy needle 260 is inserted into a container of sterile saline and the biopsy plunger flange 235 is retracted slowly drawing saline into the biopsy chamber 221. Upon filling the biopsy chamber 221 with an appropriate amount of saline, the syringe 100 is placed in a vertical orientation with the needle 260 pointing upwards and the biopsy plunger flange 235 depressed slightly to expel any air within the chamber 221. The syringe assembly 100 is then inverted and a coagulant filled syringe is attached to the check valve 140. The coagulant material, typically Gelfoam paste (1 gram/25 cc saline), is injected through the check valve 140 into the inner coagulant chamber 136. When the chamber 136 is filled, the syringe 100 is again inverted and the outer chamber 135 is filled until the Gelfoam can be observed exiting the interior channel 205 located between the outer sheath 200 and the biopsy needle 260. The Gelfoam syringe is then removed from the check valve 140 and the syringe is ready to take a biopsy.

The syringe 100 can either be placed in the delivery system 500 or used manually; the operation of the components is identical. The manual operation will be described as the operation of the delivery system was described previously. Upon identification of the proper biopsy site, the skin is pierced with the needle extended and inserted through the tissue layers into the abdominal cavity. The biopsy plunger 235 is depressed slightly to expel any tissue that may have gotten into the needle track during the insertion process. The unit is advanced until the needle 260 contacts the outer surface of the organ to be biopsied and inserted slightly. The biopsy plunger 235 is retracted slightly to provide a negative pressure in the biopsy chamber 221 and "hold" on to the surface of the biopsy material 150 within the needle channel 261. The needle 260 is further advanced into the tissue to a desired depth, usually 2 centimeters. While maintaining the negative pressure in the biopsy chamber 221, the coagulant plunger 290, along with the biopsy plunger 225 and attached needle 260, are retracted. As the coagulant plunger is retracted, FIG. 5D, the coagulant material within the inner coagulant chamber 136 and outer coagulant chamber 135 is slightly pressurized. When the biopsy needle 260 has been retracted past the diameter reduction point 220 of the sheath 200, the coagulant material will flow out through the inner channel 205 of the sheath 200 into the tissue. As the coagulant plunger 290 is retracted, the coagulant flows, following the direction of the arrows 155, rearward in the inner chamber 136 and then reverses direction as it passes through the portals 190 of the inner coagulant cylinder 160 and forward in the outer coagulant chamber 135. The coagulant finally flows outward through the inner channel 205 into the biopsy site.

With the biopsy site filled with coagulant, the needle portion of the needle assembly 100 is withdrawn from the body. The coagulant plunger is pushed back into the assembly so that the biopsy needle 260 extends out past the tip of the sheath 210. The biopsy plunger 235 is then also pushed back into the coagulant plunger 290 expelling the biopsy sample.

As described above, the coagulant can be delivered to the biopsy track by holding the needle sheath 200 stationary and injecting the coagulant through the inner channel 205. According to an alternative embodiment of the invention, the method of delivering the coagulant into the biopsy track can include withdrawing the needle sheath 200 during delivery of the coagulant in an elongated trail that follows the biopsy track. This technique places the absorbable coagulant material in a trail that fills the entire biopsy track and provides the added benefit of providing hemostasis along the entire biopsy track. This is particularly helpful for stopping the bleeding of biopsy tracks in organs that tend to have excessive bleeding such as the liver, kidney, spleen, and other vascular organs.

The absorbable coagulant may also be used to deliver a beneficial agent, such as contrast agent, thrombin, radiation treatment, or the like. The coagulant can also be used to deliver therapeutic agents, such as radioactive isotopes for localized treatment of tumors, anti-cancer agents, anti-metastatic agents, and the like. Examples of anti-cancer agents include 5-fluorouracil, cisplatin, prednisone, and others described in U.S. Pat. No. 4,619,913, which is incorporated herein by reference.

The commercially available Gelfoam material will be absorbed by the body within 1 to 6 weeks. However, the material may be designed to provide different rates of absorption. For example, Gelfoam can be designed to be absorbed at different rates by varying the degree of cross-linking. Preferably, the coagulant material is designed to be absorbed in less than one month.

The treatment of a biopsy track with an injectable absorbable coagulant to facilitate homeostasis in conjunction with procuring a biopsy provides substantial advantages in comfort over external pressure methods or the insertion of a pledget of Gelfoam foam as described in U.S. Pat No. 6,086,607. In U.S. Pat No. 6,086,607, the pledget must be inserted through a catheter previously inserted. The insertion of a catheter involves a longer procedure and the risk of the catheter shifting while the operator switches or disconnects from the aspiration biopsy syringe to the coagulant delivery syringe as described in the referenced patent. In addition, the present invention also provides advantages over the insertion of an absorbable sponge material in a dry state with an applicator. A dry piece of sponge material must be cut to the particular size of the biopsy track and does not swell to fill the track until the blood has sufficiently saturated the sponge material which can take significantly longer and provides inadequate local compression.

The present invention may be employed to deliver other materials other than coagulant material into a biopsy track or used to drain and fill an abscess. Additionally, the triggers can be replaced with a motor having exterior controls.

While the invention has been described in detail with reference to the preferred embodiments thereof, it will be apparent to one skilled in the art that various changes and modifications can be made and equivalents employed, without departing from the present invention.

What is claimed:

1. A syringe unit for obtaining a biopsy, said syringe unit comprising:
    a hollow needle;
    a needle sheath,
        said needle sheath having a diameter greater than said hollow needle and being positioned relative to hollow needle to form a hollow channel there-between;
    an outer casing, a middle coagulant cylinder and an inner coagulant cylinder,
    a coagulant chamber, said coagulant chamber being within said outer casing and being in fluid communication with said needle sheath,
    a coagulant plunger, said coagulant plunger being movable within said middle coagulant cylinder, a biopsy plunger, said biopsy plunger being movable within said coagulant plunger;
    a biopsy chamber, said biopsy chamber being in fluid communication with said hollow needle;
    wherein said biopsy is pulled into said hollow needle and a coagulant is dispelled through said needle sheath.

2. A syringe unit for obtaining a biopsy, said syringe unit comprising:
    a hollow needle;
    a needle sheath, said needle sheath having:
        a distal segment, said distal segment having a diameter greater than said hollow needle;
        a proximal region, said proximal region having a diameter greater than said distal segment;
        a transition segment, said transition segment being between said distal segment and said proximal region, said distal segment, said proximal region and said transition segment being positioned to form a channel;
    an outer casing, said outer casing having a body, a top and an interior having:

a coagulant cylinder, said coagulant cylinder having a proximal end having a flange and a distal end and a coagulant plunger to form a biopsy chamber, said biopsy chamber being in fluid communication with said hollow needle;

a middle coagulant cylinder, said middle coagulant cylinder being parallel with, and spaced from, said outer casing body and having a coagulant chamber;

a biopsy plunger, said biopsy plunger having a proximal end and a distal end and being movable within said coagulant cylinder;

an outer coagulant chamber, said outer coagulant chamber being between said outer casing body and said middle coagulant cylinder, said outer coagulant chamber being in fluid communication with said channel of said needle sheath;

an inner coagulant chamber, said inner coagulant chamber being adjacent to an inner coagulant cylinder;

an inner air chamber, said inner air chamber having an air vent to enable two way transfer of air;

passageways, said passageways enabling communication between said inner coagulant chamber and said outer coagulant chamber, wherein said biopsy is pulled into said hollow needle and a coagulant is dispelled through said needle sheath.

3. The syringe of claim 2 further comprising a check valve, said check valve being in one way communication with said inner coagulant chamber and said outer coagulant chamber to enable said inner coagulant chamber and said outer coagulant chamber to be filled with coagulant.

4. The syringe of claim 2 wherein said coagulant plunger further comprises a seal, said seal preventing communication between said inner coagulant chamber and said air chamber.

5. The syringe of claim 1 further comprising a delivery assembly, said delivery assembly comprising:

a top casing, said top casing having a first portion of a syringe receiving area;

a bottom casing, said bottom casing having a non movable handle and a pair of slide pins, each of said pair of slide pins extending from a first end of said bottom casing to a second end of said bottom casing and a second portion of a syringe receiving area;

a primary trigger, said primary trigger being proximate said non movable handle and extending into said bottom casing, a first end of said primary trigger being connected to a front slide holder, said front slide holder being movable along said pins, moving from a rest position to an active position proximate said syringe receiving area in response to movement of said primary trigger toward said non movable handle, said first slide holder being dimensioned to receive a first flange;

a secondary trigger, said secondary trigger being proximate said primary trigger and extending into said bottom casing and being connected to a secondary slide holder said secondary slide holder being movable along said pins, moving from a rest position to an active position toward said syringe receiving area in response to movement of said secondary trigger toward said non movable handle, said secondary slide holder being dimension to receive a secondary flange;

a slide holder return, said slide holder return moving said front slide holder and said secondary slide holder from said active position to said rest position;

a slidable extension, said slidable extension having a first end accessible by a user's thumb and a second end extending into said bottom casing, said second end being connected to a rear yoke, said rear yoke being movable along said pins, moving from a rest position to an active position proximate said syringe receiving area in response to movement of said slidable extension toward said syringe receiving area, said rear yoke being dimensioned to receive a flange of said biopsy plunger.

6. The syringe of claim 5 further comprising a front slide holder return, said front slide holder return being at least one spring, said at least one spring being movably positioned on each of said multiple slide pins, said front slide holder return moving said front slide holder from said active position to said rest position.

7. A biopsy and coagulant delivery system for removing a biopsy and subsequently delivery a coagulant to the biopsied area, said system having:

a syringe unit for obtaining said biopsy, said syringe unit having:

a hollow needle;

a multi section needle sheath, said multi section needle sheath having a distal segment, said distal segment having a diameter greater than said hollow needle;

a proximal region, said proximal region having a diameter greater than said distal segment;

a transition segment, said transition segment being between said distal segment and said proximal region, said distal segment, said proximal region and said transition segment forming a cavity to enable fluid communication;

an outer casing, said outer casing having a body, a top, a flange adjacent to and extending from said top, and an interior having:

a coagulant cylinder, said coagulant cylinder being movable within said casing body and having a proximal end and a distal end, said proximal end having a flange and said distal end having a cylindrical coagulant plunger, said distal end being affixed to said hollow needle;

a middle coagulant cylinder, said middle coagulant cylinder being parallel with, and spaced from, said outer casing body and having spacers at a distal end to form a coagulant chamber;

a biopsy plunger, said biopsy plunger and having a proximal end and a distal end and being movable within said coagulant plunger, said proximal end having a flange;

a biopsy chamber, said biopsy chamber being within said coagulant cylinder and having a proximal end formed by said biopsy plunger and a distal end formed by said cylindrical coagulant plunger, said biopsy chamber being in fluid communication with said hollow needle;

an outer coagulant chamber, said outer coagulant chamber being between said outer casing body and said middle coagulant cylinder and having spacers at said outer coagulant chamber distal end, said outer coagulant chamber being in fluid communication with said cavity of said needle sheath;

an inner coagulant chamber, said inner coagulant chamber being adjacent to an inner coagulant cylinder;

an inner air chamber, said inner air chamber having an air vent to enable two way transfer of air;

a coagulant plunger, said coagulant plunger being affixed to said distal end of said coagulant cylinder, said coagulant plunger being movable within said middle coagulant cylinder and having a seal, said seal preventing communication between said inner coagulant chamber and said air chamber;

passageways, said passageways being within said middle coagulant cylinder and enabling communication between said inner coagulant chamber and said outer coagulant chamber, a check valve, said check valve being in one way communication with said inner coagulant chamber and said outer coagulant chamber to enable said inner coagulant chamber and said outer coagulant chamber to be filled with coagulant;

a delivery assembly, said delivery assembly having:

a top casing, said top casing having a first portion of a syringe receiving area;

a bottom casing, Said bottom casing having a non movable handle and a pair of slide pins, each of said pair of slide pins extending from a first end of said bottom casing to a second end of said bottom casing and a second portion of a syringe receiving area;

a primary trigger, said primary trigger being proximate said non movable handle and extending into said bottom casing, a first end of said primary trigger being connected to a front yoke, said front yoke being movable along said pins, moving from a rest position to an active position proximate said syringe receiving area in response to movement of said primary trigger toward said non movable handle, said first yoke being dimensioned to receive said top flange;

a secondary trigger, a secondary trigger being proximate said primary trigger and extending into said bottom casing and being connected to a secondary yoke said secondary yoke being movable along said pins, moving from a rest position to an active position toward said syringe receiving area in response to movement of said secondary trigger toward said non movable handle, said secondary yoke being dimension to receive said flange of said coagulant cylinder;

a yoke return, said yoke return moving said front yoke and said secondary yoke from said active position to said rest position;

a slidable extension, said slidable extension having a first end accessible by a user's thumb and a second end extending into said bottom casing, said second end being corrected to a rear yoke, said rear yoke being movable along said pins, moving from a rest position to an active position proximate said syringe receiving area in response to movement of said slidable extension toward said syringe receiving area, said rear yoke being dimensioned to receive said flange of said biopsy plunger.

8. A method of taking a biopsy and subsequently delivering a coagulant to the biopsied area, comprising:

a syringe unit for obtaining said biopsy, said syringe unit comprising:

a hollow needle for removing a biopsy and a multi section needle sheath, said multi section needle sheath having a diameter greater than said hollow needle for delivery of coagulant, a body having coagulant retention and delivery means and biopsy retrieval and storage means, comprising the steps of:

filling said biopsy storage means with saline, filling said coagulant retention means with coagulant, inserting said needle and said multi section needle sheath into tissue, flushing said needle with said saline, advancing said needle into said tissue, removing said needle and said biopsied tissue, injecting said coagulant, removing said needle and said needle sheath.

9. The method of claim 8 further comprising a delivery assembly to receive said syringe, said delivery assembly having:

an interior having multiple slide pins extending from a first end of a casing to a second end of said casing and slidable yokes positioned on said slide pins, said slidable yokes being slid by a movement mechanism.

10. The method of claim 9 wherein said movement mechanism is multiple triggers, said multiple triggers being moved by a user's hand.

11. The method of claim 9 wherein said movement mechanism is motorized.

* * * * *